| United States Patent [19] | [11] Patent Number: 4,970,333 |
|---|---|
| Rabon, Jr. et al. | [45] Date of Patent: Nov. 13, 1990 |

[54] PROCESS FOR MAKING CARBOXYLIC ACID ESTERS USING A CROSSLINKED ACRYLIC RESIN AS THE CATALYST

[75] Inventors: James A. Rabon, Jr., West Columbia, Tex.; William C. Pike, Midland, Mich.; Clinton J. Boriack, Freeport, Tex.

[73] Assignee: The Dow Chemical Company, Midland, Mich.

[21] Appl. No.: 114,893

[22] Filed: Oct. 29, 1987

[51] Int. Cl.$^5$ .................... C07C 67/26; C07C 69/003; C07C 69/54

[52] U.S. Cl. ................. 560/209; 260/410.6; 560/93; 560/112; 560/200; 560/240

[58] Field of Search ................. 560/209, 240, 112, 93, 560/200, 204; 260/410.6

[56] References Cited

U.S. PATENT DOCUMENTS

| 2,630,427 | 3/1953 | Hwa | 260/86.7 |
|---|---|---|---|
| 2,862,893 | 12/1958 | Hwa | 260/2.1 |
| 2,862,894 | 12/1958 | Hwa | 260/2.1 |
| 3,340,295 | 9/1967 | Wheeler et al. | 560/240 |
| 3,427,262 | 2/1969 | Corte et al. | 260/2.2 |
| 3,551,357 | 12/1970 | Corte et al. | 260/2.1 |
| 3,791,866 | 2/1974 | Kunin et al. | 127/46 A |
| 3,804,884 | 4/1974 | Jeffrey et al. | 560/209 |
| 3,870,663 | 3/1975 | Clemens et al. | 260/25 B |
| 4,052,343 | 10/1977 | Cunningham | 260/2.1 E |
| 4,082,701 | 4/1978 | Fries et al. | 260/2.1 E |
| 4,501,826 | 2/1985 | Meitzner et al. | 521/29 |

*Primary Examiner*—Vivian Garner
*Attorney, Agent, or Firm*—Carol J. Cavender

[57] ABSTRACT

The production of esters via the reaction of an epoxide with a carboxylic acid hasbeen shown to give improved activity when a strong base macroporous anion exchange resin having an acrylic backbone is used in place of a styrene-divinylbenzene based anion exchange resin having an equivalent exchange capacity. Excellent results are obtained when acrylic acid and propylene oxide are reacted together in the presence of strong base macroporous anion exchange resins which have an acrylic backbone.

24 Claims, No Drawings

PROCESS FOR MAKING CARBOXYLIC ACID ESTERS USING A CROSSLINKED ACRYLIC RESIN AS THE CATALYST

BACKGROUND OF THE INVENTION

The preparation of esters by reacting an epoxide with a carboxylic acid is catalyzed by the use of a strongly basic anion exchange resin and is well known technology. Especially well know is the preparation of hydroxyalkyl(meth)acrylates by reacting an alkylene oxide and acrylic or methacrylio acid. The strongly basic anion exchange resin commonly employed as a catalyst in this reaction is a macroporous resin of the styrene-divinylbenzene type. The resin may be added to the reactor in any of several forms, e.g. as either the chloride or hydroxide form. One patent which describes the use of such a resin is U.S. Pat. No. 3,340,295. A resin having a particular swelling capacity in water, a particular ion exchange capacity and a limited amount of monosubstituted aromatic rings in the polymer backbone for catalyzing the subject reaction is described in U.S. Pat. No. 3,804,884.

Strongly basic anion exchange resins have also been made from polymers having an acrylic backbone, the manufacture of which is found in numerous patents. One of the earliest of these is U.S. Pat. No. 2,630,427, which teaches reacting in aqueous medium a tertiary amine, e.g. trimethylamine, with an insoluble, crosslinked copolymer of a glycidyl ester with a copolymerizable monomer containing two or three non-conjugated vinylidene groups. A later patent, U.S. Pat. No. 2,862,893, reacts the amine with a copolymer of a chlorohydrin ester and a copolymerizable monomer which contains at least two non-conjugated vinylidene groups. U.S. Pat. No. 3,427,262 teaches crosslinking the polyacrylic structure with an aliphatic or cycloaliphatic hydrocarbon containing two or more allyl groups, e.g. hexa-1,5-diene, and, optionally, an additional crosslinking agent of a di- or trivinyl aromatic compound. The product is said to be more stable and less hydrolyzable. U.S. Pat. No. 3,551,357 also discloses a process for making a hydrolysis-resistant acrylic ester-based anion exchange resin using other divinyl aromatic crosslinkers. Additionally, U.S. Pat. No. 4,052,343 discloses a polymer which has ester functionality, and U.S. Pat. No. 4,082,701 discloses a polymer having amide rather than ester functionality which is more resistant to hydrolysis.

These strongly basic acrylic-based anion exchange resins have utility in applications such as decolorizing cane sugar syrups (U.S. Pat. No. 3,791,866), recovery of uranium complexes (U.S. Pat. No. 3,870,663), removal of dyes from waste streams and chemical and oxygen demanding wastes from pulp mill effluents (U.S. Pat. No. 4,082,701).

SUMMARY OF THE INVENTION

The use of a macroporous strong base anion exchange acrylic-based resin as a catalyst for the production of hydroxyalkyl esters, via the reaction of an epoxide with a carboxylic acid, has been shown to give improved activity when compared to a styrenedivinylbenzene-based strong base anion exchange resin having an equivalent dry weight exchange capacity.

DETAILED DESCRIPTION OF THE INVENTION

Strong base anion exchange resins having an acrylic backbone, such as the macroporous anion exchange resins designated Amberlite* IRA-958 and Lewatit** AP-247-A which are commercially available, are useful in the esterification reaction. Such resins can have a dry weight exchange capacity (DWC) of from about 1.5 to about 4.4 meq of exchangeable chloride per gram dried resin. Such macroporous resins are crosslinked with from about 2 to 10 percent of a crosslinking monomer. When employed as catalysts in the esterification reaction wherein a carboxylic acid and an epoxide are reacted, the activity of such resins under certain specified conditions will provide at least about a 60 percent conversion of acid with >98 percent selectivity to hydroxyalkyl acrylate.

* A trademark of Rohm & Haas Company.
** A trademark of Mobay Corporation.

Outside the dry weight exchange capacities indicated above, the rate of reaction decreases, either because the number of reactive sites is too small at the lower end of the DWC range or because the sites are too crowded and unavailable to the reactants at the higher capacities. Outside the crosslinked ranges indicated above, the resins either lose swelling ability at the higher levels of crosslinking or lose mechanical properties at the lower levels.

Epoxides which can be employed as reactants in the esterification reaction include alkylene oxides such as ethylene oxide (EO), propylene oxide (PO), 1,2- or 2,3-butylene oxides, hexene, cyclohexene and octene oxides and epoxides such as epichlorohydrin and styrene oxide.

Acids which can be esterified using the anion exchange resin catalysts of the invention are the unsaturated mono- and dicarboxylic acids having from 3 to 5 carbon atoms, e.g. acrylic (AA), methacrylic, fumaric, maleic and itaconic. Saturated monocarboxylic acids having from about 2 to about 20 carbon atoms, e.g. acetic, propanoic, butanoic, hexanoic acids, capric (10 carbons), myristic (14 carbons), palmitic (16 carbons), stearic (18 carbons) and the like and dicarboxylic acids, having from about 2 to about 12 carbon atoms, e.g. oxalic, succinic, adipic and the like are useful. Aromatic mono- and dicarboxylic acids, such as benzoic and the isomeric phthalic acids can also be esterified by the process of the invention.

Molar ratios of epoxide to acid in the feed to the reactor are operable at from about 1.2/1 to about 20/1, but ratios of from about 3/1 to about 12/1 are preferred. The molar ratio in the reactor, however, will change as the acid reactant is used up, becoming ever higher in favor of the oxide reactant. In a continuous reaction, the mole ratio of the reactants in the reactor will be determined by feed ratios and the particular conversion achieved.

The esterification reaction can be conducted in a stirred-batch reactor or in a fixed or fluid bed reactor. It is conducted at a temperature of from about 50° to about 110° C., preferably from about 60° to about 90° C. Below the operable range of temperature the reaction becomes impractically slow and above the temperature range, polymerization of the reactants and/or product becomes a competing reaction.

Autogenous pressure, which depends upon the particular reactants and temperature at which the reaction is conducted, is generally employed. The pressure employed, however, must be sufficient to keep the reactants in the liquid phase. This, of course, is a problem primarily found with the lower molecular weight epoxides which have low boiling points.

The reaction may be conducted in a solvent if desired, although the excess of epoxide generally serves as a diluent. Solvents suitable for the reaction include inert aliphatic or aromatic hydrocarbons, e.g. hexane, petroleum ether and xylene.

The strong base anion exchange resin employed as the catalyst may be fed to the reactor in the form of the halide, hydroxide, alkoxide or carboxylic acid salt, but is preferably used in the form of the chloride or of the carboxylate anion of the particular acid employed as reactant.

The following are representative examples of the invention, together with comparative examples using styrene-divinylbenzene anion exchange resins of the art. These were conducted in a batch reactor in which HPA or HEA was added to simulate the composition of a reaction mixture one would encounter in a continuous process for producing those esters. In all examples, both of the invention and comparative, the resin was dried at 50° C. under vacuum for 18 hrs. prior to use in the reaction.

EXAMPLE 1

Into a stainless steel cylinder (300 mL), fitted with a rupture disc and appropriate valves, was introduced 5.0 g of a strong base anion exchange resin (Amberlite IRA-958)*, acrylic acid, hydroxypropyl acrylate(HPA) and propylene oxide. This catalyst had a 4.1 DWC. The cylinder was sealed and placed in a shaker bath at a temperature of 80° C. and allowed to react for 40 min. The cylinder was then removed from the shaker bath, opened and the reaction mixture removed without removing the catalyst resin beads. This procedure was then repeated four times to allow the catalyst to age and the activity to reach a constant level. After each run the reaction mixture was stripped of excess PO under vacuum and any residual acid remaining determined by titration with a standard sodium hydroxide solution. A run made after the catalyst had levelled out, using 5.0 g AA, 42.6 g HPA and 142.2 g PO, indicated that 65.7% of the AA had been converted to HPA.

In another run, made in the same manner except for the use of a strong base styrene-divinylbenzene anion exchange resin which had the same DWC, i.e. 4.1, the conversion of AA to HPA was only 41.8 percent.

EXAMPLE 2

In another example a different anion exchange resin having an acrylic backbone (Lewatit AP-247-A) was employed. The procedure was the same as in Example 1, again employing 5.0 g of catalyst, AA, PO and HPA. The catalyst was 8% crosslinked with a DWC of 2.1 and was dried as before prior to its use as a catalyst. The reaction mixture, in the presence of the catalyst, was heated at a temperature of 80° C. for 40 min. After several runs to level out the performance of the catalyst (as before), a run was made employing 5.0 g (0.069 M) AA, 42.75 g (0.329 M) HPA and 142.05 g (2.45 M) PO. The conversion of AA to HPA was 53.9%.

EXAMPLE 3

An esterification was conducted to make hydroxyethyl acrylate (HEA). Using the same strong base anion exchange resin and the same procedure as in Example 1, HEA(48.18 g, 0.415 M), AA(6.3 g, 0.087 M) and ethylene oxide (EO)(143.3 g, 3.26 M) were reacted in the presence of 12.8 g. of the resin for 20 min. at 68° C. After repeating the run four times (as before) to bring the activity to a constant level, a run employing the amounts of reactants and catalyst indicated above gave a conversion of AA to HEA of 59.3 percent.

We claim:

1. In the process of reacting a carboxylic acid with an epoxide to form a hydroxyalkyl ester by conducting the reaction in the presence of a strong base anion exchange resin, the improvement which comprises employing a strong base macroporous anion exchange resin having an acrylic backbone.

2. The process of claim 1 wherein the anion exchange resin has from about 2 to about 10 percent crosslinking.

3. The process of claim 2 wherein the dry weight exchange capacity is from about 1.5 to about 4.4 meq/g.

4. The process of claim 3 wherein the reactant epoxide is employed in a molar excess.

5. The process of claim 4 wherein the mole ratio of epoxide reactant to that of the carboxylic acid reactant is in the range of from about 1.2/1 to about 20/1.

6. The process of claim 5 wherein the epoxide reactant is an alkylene oxide.

7. The process of claim 6 wherein the carboxylic acid is an unsaturated acid.

8. The process of claim 7 wherein the molar ratio of alkylene oxide to unsaturated acid is from about 3/1 to about 12/1.

9. The process of claim 7 wherein the alkylene oxide contains from 2 to 8 carbon atoms.

10. The process of claim 9 wherein the molar ratio of alkylene oxide to unsaturated acid is from about 3/1 to about 12/1.

11. The process of claim 8 wherein the unsaturated acid contains 3 to 6 carbon atoms.

12. The process of claim 11 wherein the molar ratio of alkylene oxide to unsaturated acid is from about 3/1 to about 12/1.

13. The process of claim 11 wherein the alkylene oxide is ethylene oxide.

14. The process of claim 13 wherein the unsaturated acid is acrylic acid.

15. The process of claim 13 wherein the unsaturated acid is methacrylic acid.

16. The process of claim 11 wherein the alkylene oxide is propylene oxide.

17. The process of claim 16 wherein the unsaturated acid is methacrylic acid.

18. The process of claim 16 wherein the unsaturated acid is acrylic acid.

19. The process of claim 11 wherein the oxide is butylene oxide.

20. The process of claim 19 wherein the unsaturated acid is acrylic acid.

21. The process of claim 19 wherein the unsaturated acid is methacrylic acid.

22. The process of making a hydroxyalkyl carboxylic acid ester by reacting a carboxylic acid with an epoxide in the presence of a catalyst which is a strong base macroporous anion exchange resin having an acrylic backbone.

23. The process of claim 22 wherein the dry weight exchange capacity of the catalyst resin is from about 1.5 to about 4.4 meq/g.

24. The process of claim 23 wherein the crosslinking is from about 2 to about 10 percent.

* * * * *